United States Patent [19]
Grattan

[11] Patent Number: 5,866,162
[45] Date of Patent: Feb. 2, 1999

[54] PHARMACEUTICAL COMPOSITION CONTAINING A DRUG/β-CYCLODEXTRIN COMPLEX IN COMBINATION WITH AN ACID-BASE COUPLE

[75] Inventor: Timothy James Grattan, Guildford, England

[73] Assignee: SmithKline Beecham p.l.c., Brentford, United Kingdom

[21] Appl. No.: 827,625

[22] Filed: Apr. 9, 1997

Related U.S. Application Data

[63] Continuation of Ser. No. 458,148, filed as PCT/EP94/02515, Jul. 29, 1994 published as WO95/04528, Feb. 16, 1995, abandoned.

[51] Int. Cl.⁶ .............................. A61K 9/14; A61K 9/16; A61K 9/46
[52] U.S. Cl. ........................... 424/466; 424/465; 424/489
[58] Field of Search .................................... 424/466, 440, 424/489, 439, 464, 465

[56] References Cited

U.S. PATENT DOCUMENTS

| | | | |
|---|---|---|---|
| 4,762,702 | 8/1988 | Gergely et al. | 424/44 |
| 5,019,563 | 5/1991 | Hunten et al. | 514/58 |
| 5,024,997 | 6/1991 | Motola et al. | 514/58 |
| 5,037,657 | 8/1991 | Jones et al. | 424/466 |

FOREIGN PATENT DOCUMENTS

| | | |
|---|---|---|
| 0268215 | 5/1988 | European Pat. Off. . |
| 0274444 | 7/1988 | European Pat. Off. . |
| 313328 | 4/1989 | European Pat. Off. . |
| 346006 | 12/1989 | European Pat. Off. . |
| 0490193 | 6/1992 | European Pat. Off. . |
| WO92/09308 | 6/1992 | WIPO . |

*Primary Examiner*—Thurman K. Page
*Assistant Examiner*—James M. Spear
*Attorney, Agent, or Firm*—Dara L. Dinner; Stephen Venetianer

[57] ABSTRACT

A pharmaceutical composition for oral consumption in liquid form is provided, characterized in that the composition contains a drug, preferably a lipophilic NSAID, complexed to β-cyclodextrin in a formulation also containing an acid-base couple, preferably an effervescent acid-base couple. The weight of the acid-base couple is greater than 1% of the weight of water in which the composition is to be dissolved, and provides an acid or neutral pH.

40 Claims, No Drawings

PHARMACEUTICAL COMPOSITION CONTAINING A DRUG/β-CYCLODEXTRIN COMPLEX IN COMBINATION WITH AN ACID-BASE COUPLE

This is a continuation of application Ser. No. 08/458,148, filed Jun. 1, 1995 now abandoned, which is a continuation of §371 national stage entry application Ser. No. 08/591,513, filed Jul. 29, 1994, which is a continuation of PCT/EP94/02515, filed Jul. 29, 1994, published as WO95/04528, Feb. 16, 1995.

This invention relates to a pharmaceutical composition containing a drug which is lipophilic and has poor water solubility in the form of a clathrate complex, a process for its preparation, and a palatable formulation thereof suitable for oral consumption. In particular, the invention relates to a composition containing a non-steroidal anti-inflammatory (NSAID) drug as a cyclodextrin clathrate complex suitable for oral consumption in aqueous solution.

The group of non-steroidal antiinflammatory agents (NSAIDs) includes drugs such as ibuprofen, naproxen and ketoprofen which have utility in providing relief from pain and inflammation associated with a wide range of disorders including for example chronic disease states such as arthritis. Ibuprofen is also widely indicated for the treatment of symptoms associated with the common cold and flu. Formulation of these and other poorly water-soluble drugs into preparations suitable for oral administration, in particular into water-soluble forms suitable for liquid dosing, is often complicated by the physical characteristics of the drugs which include poor water solubility, irritating odour and unpleasant taste. It is an object of the present invention to provide a palatable pharmaceutical composition containing a lipophilic, poorly water-soluble drug, for example an NSAID such as ibuprofen, naproxen or ketoprofen, formulated for oral dosing as an aqueous solution.

The ability of drug-cyclodextrin complexes to enhance water solubility and to mask unpleasant taste and odour has been known for many years. In this respect, NSAID's such as ibuprofen have proved to be very suitable as candidates for complexation with cyclodextrins.

Japanese patent publication, JP 56-46837 (Kowa Yakuhin Kogyo) discloses a method for the preparation of an ibuprofen-β-cyclodextrin clathrate complex involving the combination of ibuprofen with β-cyclodextrin in water at elevated temperature and isolation of the clathrate by spray-drying. This method is reported to yield a product containing a high percentage of ibuprofen with a molar ratio of ibuprofen to β-cyclodextrin in excess of 0.7. The increase in water solubility of the drug is considerable, being raised more than 8-fold from 10.44 mg per 100 ml to 89.38 mg per 100 ml at 27° C.

The water solubility achieved by complexation with β-cyclodextrin, although significant, is not considered sufficient to permit formulation of ibuprofen as a soluble dosage form for oral administration in liquid form wherein ibuprofen is present at a therapeutic dosage level (200–600 mg) in a suitable volume of water (50–250 ml).

European patent publication 274 444 (Bristol Myers) describes the preparation of ibuprofen-cyclodextrin complexes using (α-cyclodextrin, γ-cyclodextrin or a methylated β-cyclodextrin in place of β-cyclodextrin. The water solubility of the ibuprofen-cyclodextrin complex is further enhanced to levels of practical utility using these forms of cyclodextrin, but the high cost of these materials, reflected in the cost of medicinal products containing them, is unlikely to promote their widespread use in analgesic products, more particularly in products available for self medication for the treatment of minor aches and pains and the symptomatic relief of colds and flu.

United Kingdom patent publication GB 2,189,994 (Zambon) discloses an effervescent water-soluble ibuprofen formulation comprising ibuprofen plus arginine or a mixture of arginine and lysine and an effervescent couple in the form of sodium or potassium bicarbonate and sodium bitartrate.

U.S. Pat. No. 4,762,702 (Gergely) discloses a pharmaceutical preparation in which ibuprofen particles are enveloped by a coating of a hydro-colloid and fumaric acid which is intended to reduce the irritant effects of orally ingested ibuprofen. An effervescent formulation incorporating citric acid and calcium carbonate into the preparation is also described.

United Kingdom patent publication GB 2,219,585 (Reckitt & Colman) discloses a complex of β-cyclodextrin with the sodium, potassium, ammonium, magnesium, calcium, arginine, glycine or lysine salt of ibuprofen, having a molar ratio of ibuprofen to β-cyclodextrin in the range 1:0.2 to 1:0.75. The complexes may be formulated with a buffer system or an effervescent couple incorporating a pharmaceutically acceptable acid salt- to provide a pH in the range 6 to 8 on reconstitution with water.

European patent publication 0 490 193 (Medica Chem-Pharm) discloses complexes of the active enantiomer of ibuprofen and/or its physiologically tolerated salts with a cyclodextrin and/or a cyclodextrin derivative. Although there is disclosed an ibuprofen effervescent tablet formulation, it is not soluble in the volume of water needed to form a therapeutically acceptable composition.

International Patent Application PCT/GB93/00702 (SmithKline Beecham) overcomes the problem of poor solubility of ibuprofen by reconstituting an ibuprofen/β-cyclodextrin complex in hot water to provide a pleasant tasting soluble liquid presentation. It was found that an approximately 30-fold increase in solubility could be achieved by dosing an ibuprofen-β-cyclodextrin complex in aqueous solution at elevated temperatures and thereby achieve therapeutic dosage levels of ibuprofen in solution in a single-dose liquid formulation.

The present invention provides a further drug-cyclodextrin complex formulation which is suitable for administration as an aqueous solution, and which is palatable and inexpensive to manufacture. The formulation according to the present invention provides a therapeutically active dose of the drug as a complex with β-cyclodextrin. The formulation is suitable for reconstitution with cold water and provides a pleasant tasting solution at acid or neutral pH.

It has been found that when formulated in the presence of an acid-base couple, preferably an effervescent acid-base couple, a drug/β-cyclodextrin complex, which in isolation is soluble in water only at elevated temperatures, has enhanced solubility and dissolves in cold water to provide a therapeutic drug dose as a single-dose, liquid formulation.

According to the present invention there is provided a pharmaceutical composition for oral consumption in aqueous solution comprising a drug/β-cyclodextrin complex, characterised in that the composition further comprises a pharmaceutically acceptable acid-base couple, preferably an effervescent acid-base couple, in a quantity sufficient to cause the drug/β-cyclodextrin complex to dissolve when the composition is mixed with cold water and provide a solution with acid or neutral pH.

Suitable non-effervescent acid-base couples for use in the invention are those commonly known in the art, for example a combination of a water soluble acid and a conjugate base in the form of a sodium or potassium salt. Suitable effervesent couples are also commonly known in the art, for example a combination of one or more water soluble acidic substances with one or more basic compounds which liberate carbon dioxide on neutralisation with acid.

Examples of suitable acids for use in the invention include, tartaric acid, citric acid, ascorbic acid and other edible organic acids. Suitable salts of organic acids include mono- di- and tri-basic salts, for example monosodium citrate, trisodium citrate, monosodium tartrate, trisodium tartrate and other salts of edible organic acids. Inorganic acidic substances such as monosodium phosphate are also suitable components of acid-base couples. Examples of suitable bases for use in the invention include sodium carbonate, percarbonate and bicarbonate, and other alkali metal and alkali earth metal carbonates, percarbonates and bicarbonates, and mixed carbonate salts, such as sodium glycine carbonate and potasium glycine carbonate.

The preferred acid-base couple for this invention is an effervescent couple which contains citric and/or tartaric acid and sodium bicarbonate and/or carbonate.

The amount of couple required to solubilise the drug/$\beta$-cyclodextrin complex will depend on the amount and type of drug used. However a minimum level of couple considered acceptable in a composition of the invention is an amount such that the weight of couple is greater than about 1% of the weight of water in which it is designed to be reconstituted or is greater than 1% of the weight of water in which it is to be dissolved, ie the final concentration of the couple on reconstitution in water (not allowing for loss of carbon dioxide for effervescent couples) should be greater than about 1% by weight. Levels below this amount are generally considered unsuitable since, on reconstitution with water, incomplete dissolution of the drug/$\beta$-cyclodextrin occurs. The maximum level of couple considered acceptable in a composition of the invention is 15% of the weight of water in which it is to be reconstituted. For effervescent compositions, levels in excess of this amount tend to lead to excessive effervescence, resulting in overflow of liquid from the glass or beaker and loss of some of the formulation. In addition high levels of acid-base couple tend to impart a salty taste to the palate. Compositions of the present invention are suitably administered as pleasant tasting solutions in the pH range 4.0 to 7.0.

The constituents of acid-base couples suitable for use in compositions of the invention and their relative amounts may be selected using principles well known in the art of pharmaceutical drug formulation. An acid-base couple for use in compositions of the invention may be designed so that the final pH of the formulation following reconstitution with water is in the range of 4.0–7.0 and preferably in the range of 5.0–6.5. The pH of solutions resulting from reconstitution of the couple in water may be adjusted by altering the ratio of the alkali and acid components of the couple. If the couple is designed so that the final pH of the formulation following reconstitution with water falls below the specified range there may be a tendency for the drug/$\beta$-cyclodextrin clathrate to precipitate, which detracts from the appearance and palatibility of the product. If the couple is designed to so that the final pH following reconstitution is above the specified-range then the solution will impart an alkaline/soapy taste.

Preferred drugs for use in the compositions of the present invention include lipophilic NSAID's, for example propionic acid derivatives such as ibuprofen, naproxen and ketoprofen.

Accordingly, drug/$\beta$-cyclodextrin clathrates which are suitable for use in this invention include ibuprofen/$\beta$-cyclodextrin clathrates, naproxen/$\beta$-cyclodextrin clathrates, ketoprofen/$\beta$-cyclodextrin clathrates and clathlerates of $\beta$-cyclodextrin with other propionic acid type NSAID's. In addition, the invention may use clathrates of $\beta$-cyclodextrin with salts of ibuprofen, naproxen and other propionic acid type NSAID's, for example metal salts, such as sodium, potassium, magnesium, and calcium, or amino-acid salts such as arginine, ornithine or lysine.

The drugs according to this invention may be as either the racemate or enantiomers. Any reference to the drug is intended to cover all active forms and may be either in the R or S enantiomer or racemate form.

The molar ratio of $\beta$-cyclodextrin to drug (or drug salt) may be in the range 0.8:1 to 10:1, suitably in the range 1:1 to 10:1, more suitably in the range 1:1 to 5:1 and preferably in the range 1:1 to 3:1. If the ratio falls below this range, an insufficient amount of the drug will be complexed which will lead to a deterioration in taste properties of the final product, and undissolved drug following reconstitution with water. If the amount of cyclodextrin is excessive then, for effervescent formulations, there is a tendency for excessive foam formation on mixing the formulation with water which may lead to loss of some of the formulation. Furthermore, it is for economic reasons considered desirable to minimise the amount of cyclodextrin used in the composition.

The invention also provides a process for the preparation of a pharmacetical composition of the invention which process comprises the admixture of a drug/$\beta$-cyclodextrin clathrate complex and an acid-base couple.

A drug/$\beta$-cyclodextrin complex may be prepared by heating the drug and $\beta$-cyclodextrin in water or in a buffered aqueous solution, suitably to a temperature of 100° C., followed by crystallisation of the drug/$\beta$-cyclodextrin complex from the solution thus formed, suitably by maintaining the solution in the temperature range $-5°$ to 20° C. Alternatively a drug/$\beta$-cyclodextrin complex may be made by any other method known in the art, for example by a co-precipitation or kneading method or by spray-drying a solution of the drug and $\beta$-cyclodextrin.

The acid-base couple may be prepared by any method known in the art, for example by dry mixing the components of the couple in a suitable mixer, or by granulation using a rotary granulator, fluid-bed granulator or other suitable granulator, followed by drying to remove residual moisture. If granulation is the chosen method of preparation, other components of the formulation may be included into the granulation step, for example part, or all of the drug/$\beta$-cyclodextrin clathrate, flavours, sweeteners and colours.

A composition of the invention may be formulated in any convenient form, for example as a tablet for solution, or alternatively in powder or granular form for reconstitution with water or as a ready-to-drink preparation.

Compositions of the invention may be formulated with any appropriate carrier or adjuvant appropriate to the chosen dosage form. Thus, compositions of the invention may include for example preservatives, suspending agents, wetting agents, flavouring agents, bulking agents, binders, adhesives, lubricants, disintegrants, colouring agents, sweetening agents, adsorbents, thickeners and diluents, appropriate to their form.

Compositions of the invention containing a drug/$\beta$-cyclodextrin complex and an acid-base couple may in addition include additional pharmaceutical agents suitable for administration therewith which are not complexed with $\beta$-cyclodextrin, including for example analgesics, antiinflammatories and antipyretics and also expectorants, antihistamines, decongestants and antitussive agents, such as for example phenypropanolamine, phenylephrine, pseudoephedrine, dextromethorphan, caffeine, codeine and ascorbic acid.

The following Examples (1 to 18) are illustrative of the invention. Examples (A to G) are outside the scope of the invention but are included to further S demonstrate aspects of the invention.

In the Examples, unless otherwise stated, the abbreviation βCD refers to β-cyclodextrin undecahydrate (β-cyclodextrin. $11H_2O$).

EXAMPLE 1
Preparation of βCD/Ibuprofen Clathrate (1.1:1)

βCD (146.6 g, 110 mM) was dissolved in water (1000 ml) at 100° C. Ibuprofen (20.6 g, 100 mM) was added and the resulting solution was cooled to 1° C. to give a white crystalling precipitate which was washed with cold water and dried at 50° C. for 4 hours in a convection oven. The product, a white solid, was sieved through a 500 μm screen to yield 125 g of βCD/ibuprofen clathrate, containing about 14% ibuprofen.

(400 mg ibuprofen per 2857 mg of clathrate).

EXAMPLE 2
Preparation of an effervesent pharmaceutical composition containing Ibuprofen/βCD clathrate for reconstitution with cold water Ingredients 2 and 3 were seived through a 500 μm screen and mixed in a suitable mixer for 5 minutes. A small aliquot of water was added and the product was mixed for a further 5 minutes and then placed on stainless steel trays and dried for 2 hours at 60° C. The resulting granule was sieved through a 500 μm screen mixed for 5 minutes with ingredient 1 and then filled into sachets, (target fill weight 10.85 g) with each sachet containing the equivalent of 400 mg ibuprofen.

| 1. Ibuprofen/βCD clathrate from example 1 | 57.14 g |
|---|---|
| 2. Sodium bicarbonate | 100.00 g |
| 3. Citric acid (anhydrous) | 60.00 g |

The powder from one of the sachets was added to 200 ml of cold water (15° C.) to give an effervescent, pleasant tasting, clear solution, which contained 400 mg ibuprofen/200 ml of water at a pH of approximately 6.3.

EXAMPLE 3
Preparation of an effervesent pharmaceutical composition containing Ibuprofen/βCD clathrate for reconstitution with cold water Ingredients 2 and 3 were seived through a 500 μm screen and mixed in a suitable mixer for 5 minutes. A small aliquot of water was added and the product was mixed for a further 5 minutes and then placed on stainless steel trays and dried for 2 hours at 60° C. The resulting granule was sieved through a 500 μm screen mixed for 5 minutes with ingredients 1 and 4 and then filled into sachets, (target fill weight 6.428 g) with each sachet containing the equivalent of 200 mg ibuprofen.

| 1. Ibuprofen/βCD clathrate from example 1 | 71.4 g |
|---|---|
| 2. Sodium bicarbonate | 116.0 g |
| 3. Citric acid (anhydrous) | 109.0 g |
| 4. Sodium carbonate (anhydrous) | 25.0 g |

The powder from one of the sachets was added to 150 ml cold water (16° C.) to give an effervescent, pleasant tasting, clear solution, which contained 200 mg ibuprofen/150 ml of water at a pH of approximately 6.0.

EXAMPLE 4
Preparation of βCD/Naproxen Clathrate (1.8:1)

β-cyclodextrin (120.3 g, 90 mM) was dissolved in water (500 ml) at 100° C. Naproxen (11.5 g 50 mM) was added and the resulting solution was cooled to 1° C. to give a white precipitate, which was dried at 60° C. in a convection oven for 16 hours. The product, a white solid, was sieved through a 500 μm screen to yield 110 g of βCD/naproxen clathrate, containing about 9.4% naproxen.

EXAMPLE 5
Preparation of βCD/Naproxen Clathrate (1.1:1)

β-cyclodextrin (294 g, 220 mM) was dissolved in water (1500 ml) at 100° C. Naproxen (46 g 200 mM) was added and the resulting mixture was stirred for 1 hour at 95° C. and then cooled, with stirring, to 1° C. to give a white precipitate, which was dried at 60° C. in a convection oven for 16 hours. The product, a white solid, was sieved through a 250 μM screen, to yield 250 g of βCD/naproxen clathrate, containing about 15.3% naproxen.

EXAMPLE 6
Preparation of an effervescent pharmaceutical composition containing Naproxen/βCD clathrate for reconstitution with cold water Ingredients 2 and 3 were seived through a 500 μm screen and mixed in a suitable mixer for 5 minutes. A small aliquot of water was added and the product was mixed for a further 5 minutes and then placed on stainless steel trays and dried for 2 hours at 60° C. The resulting granule was sieved through a 500 μm screen, mixed for 5 minutes with ingredients 1 and 4, and then filled into sachets, (target fill weight 7.38 g) with each sachet containing the equivalent of 200 mg naproxen

| 1. Naproxen/βCD clathrate from example 4 | 106.0 g |
|---|---|
| 2. Sodium bicarbonate | 116.0 g |
| 3. Citric acid (anhydrous) | 109.0 g |
| 4. Sodium carbonate (anhydrous) | 25.0 g |

The powder from one of the sachets was added to 150 mls cold water (15° C.) to give an effervescent, pleasant tasting, clear solution, which contained 200 mg naproxen/150 ml of water at a pH of approximately 6.0.

EXAMPLE 7
Preparation of an effervescent pharmaceutical composition containing Naproxen/βCD clathrate for reconstitution with cold water Ingredients 2 and 3 were seived through a 500 μm screen and mixed in a suitable mixer for 5 minutes. A small aliquot of water was added and the product was mixed for a further 5 minutes and then placed on stainless steel trays and dried for 2 hours at 60° C. The resulting granule was sieved through a 500 μm screen, mixed for 5 minutes with ingredients I and 4, and then filled into sachets, (target fill weight 6.307 g) with each sachet containing the equivalent of 200 mg naproxen.

| 1. Naproxen/βCD clathrate from example 5 | 65.5 g |
|---|---|
| 2. Sodium bicarbonate | 116.0 g |
| 3. Citric acid (anhydrous) | 109.0 g |
| 4. Sodium carbonate (anhydrous) | 25.0 g |

The powder from one of the sachets was added to 150 mls cold water (15° C.) to give an effervescent, pleasant tasting, clear solution, which contained 200 mg naproxen/150 ml of water at a pH of approximately 6.0.

EXAMPLE 8
Preparation of an effervescent pharmaceutical composition containing Naproxen/βCD clathrate for reconstitution with cold water Ingredients 2 and 3 were seived through a 500 μm screen and mixed in a suitable mixer for 5 minutes. A small aliquot of water was added and the product was mixed for a further 5 minutes and then placed on stainless steel trays and dried for 2 hours at 60° C. The resulting granule was sieved through a 500 μm screen, mixed for 5 minutes with ingredients 1 and 4, and then filled into sachets, (target fill weight 7.614 g) with each sachet containing the equivalent of 400 mg naproxen.

| 1. Naproxen/βCD clathrate from example 5 | 130.7 g |
|---|---|
| 2. Sodium bicarbonate | 116.0 g |
| 3. Citric acid (anhydrous) | 109.0 g |
| 4. Sodium carbonate (anhydrous) | 25.0 g |

The powder from one of the sachets was added to 200 mls cold water (15° C.) to give an effervescent, pleasant tasting, clear solution, which contained 400 mg naproxen/200 ml of water at a pH of approximately 6.0.

EXAMPLE 9
Preparation of βCD/Naproxen sodium Clathrate (1.1:1)

β-cyclodextrin (147 g, 110 mM) was dissolved in water (500 ml) at 100° C. Naproxen sodium (25.2 g 100 mM) was added and the resulting solution was stirred or 1 hour at 95° C. and then poured onto trays and evaporated to dryness in a convection oven at 60° C. The product, a white amorphous solid, was sieved through a 250 μm screen, to yield 123 g of βCD/naproxen clathrate, containing about 15.1% naproxen.

EXAMPLE 10
Preparation of an effervescent pharmaceutical composition containing Naproxen sodium/βCD clathrate for reconstitution with cold water Ingredients 2 and 3 were seived through a 500 μm screen and mixed in a suitable mixer for 5 minutes. A small aliquot of water was added and the product was mixed for a further 5 minutes and then placed on stainless steel trays and dried for 2 hours at 60° C. The resulting granule was sieved through a 500 μm screen, mixed for 5 minutes with ingredients 1 and 4, and then filled into sachets, (target fill weight 6.325 g) with each sachet containing the equivalent of 200 mg naproxen.

| 1. Naproxen sodium/βCD clathrate from example 9 | 66.3 g |
|---|---|
| 2. Sodium bicarbonate | 116.0 g |
| 3. Citric acid (anhydrous) | 109.0 g |
| 4. Sodium carbonate (anhydrous) | 25.0 g |

The powder from one of the sachets was added to 150 mls cold water (15° C.) to give an effervescent, pleasant tasting, clear solution, which contained 200 mg naproxen/150 ml of water at a pH of approximately 6.0.

EXAMPLE 11
Preparation of a non-effervescent pharmaceutical composition containing Naproxen/βCD clathrate for reconstitution with cold water Ingredients 2 and 3 were mixed together in a suitable mixer for 5 minutes and the resulting powder was filled into sachets, (target weight 5510 mg), with each sachet containing the equivalent of 200 mg naproxen.

| 1. Naproxen/BCD clathrate | 13.1 g |
|---|---|
| 2. Tri-sodium citrate | 40.0 g |
| 3. Citric acid (anhydrous) | 2.0 g |

The powder from one of the sachets was added to 250 ml of cold water (15° C.) and stirred for 1 minute to give a non-effervescent, clear solution, which contained 200 mg naproxen/150 ml water at a pH of approximately 6.2.

EXAMPLE 12
Preparation of βCD/Ketoprofen Clathrate (5:1)

β-cyclodextrin (53.3 g, 40 mM) was dissolved in water (200 ml) at 100° C. Ketoprofen (2.05 g, 8 mM) was added and the resulting mixture was stirred for 1 hour at 95° C. and then cooled, with stirring, to 1° C. to give a white precipitate, which was dried at 60° C. in a convection oven for 16 hours. The product, a white solid, was sieved through a 250 μM screen to yield 50.4 g of βCD/ketoprofen clathrate, containing about 3.8% ketoprofen.

EXAMPLE 13
Preparation of an effervescent pharmaceutical composition containing Ketoprofen/βCD clathrate for reconstitution with cold water Ingredients 2 and 3 were sieved through a 500 μm screen and mixed in a suitable mixer for 5 minutes. A small aliquot of water was added and the product was mixed for a further 5 minutes and then placed on stainless steel trays and dried for 2 hours at 60° C. The resulting granule was sieved through a 500 μm screen, mixed for 5 minutes with ingredients 1 and 4, and then filled into sachets, (target fill weight 6.316 g) with each sachet containing the equivalent of 50 mg ketoprofen.

| 1. Ketoprofen/βCD clathrate from example 12 | 26.3 g |
|---|---|
| 2. Sodium bicarbonate | 116.0 g |
| 3. Citric acid (anhydrous) | 109.0 g |
| 4. Sodium carbonate (anhydrous) | 25.0 g |

The powder from one of the sachets was added to 150 mls cold water (15° C.) to give an effervescent, pleasant tasting, clear solution, which contained 50 mg ketoprofen/150 ml of water at a pH of approximately 6.0.

EXAMPLE 14
Preparation of a ready made effervescent pharmaceutical composition containing β-cyclodextrin/naproxen clathrate (1.1:1)

| 1. β-cyclodextrin/naproxen clathrate | 13.3 g |
|---|---|
| 2. Trisodium citrate | 29.0 g |
| 3. Sodium carbonate | 3.0 g |
| 4. Methyl paraben sodium | 3.0 g |
| 5. Deionised water | to 200 ml |

Ingredients 1, 2, 3 and 4 were dissolved in item 5. 20 ml volumes of the solution were dispensed into 250 ml bottles containing 130 ml carbonated water, mixed and then fitted with air tight closures. Each bottle contained the equivalent to approximately 200 mg naproxen in a solution of pH approximately 6.0.

EXAMPLE 15
Preparation of βCD/Naproxen Clathrate (0.9:1)

β-cyclodextrin (48.0 g, 36 mmoles) and naproxen (9.2 g, 40 mmoles) were added to 300 ml deionised water. The mixture was stirred for 1 hour at 95°–100° C. and then cooled to 1° C. to give a white precipitate, which was dried at 60° C. in a convection oven for 16 hours. The product, a white solid, was sieved through a 500 μm screen, to yield 37.6 g of βCD/naproxen clathrate, containing about 19% naproxen.

EXAMPLE 16
Preparation of a ready made effervescent pharmaceutical composition containing β-cyclodextrin/naproxen clathrate (0.9:1)

| | |
|---|---|
| 1. β-cyclodextrin/naproxen clathrate | 10.52 g |
| 2. Trisodium citrate | 29.0 g |
| 3. Sodium carbonate | 3.0 g |
| 4. Methyl paraben sodium | 3.0 g |
| 5. Deionised water | to 200 ml |

Ingredients 1, 2, 3 and 4 were dissolved in item 5. 20 ml volumes of the solution were dispensed into 250 ml bottles containing 130 ml carbonated water, mixed and-then fitted with air tight closures. Each bottle contained the equivalent to approximately 200 mg naproxen in a solution of pH approximately 6.0.

EXAMPLE 17
Preparation of an effervescent pharmaceutical composition containing β-cyclodextrin/naproxen clathrate (1.1:1) without precomplexation

| | |
|---|---|
| 1. β-cyclodextrin | 12.8 g |
| 2. Naproxen | 2.0 g |
| 3. Trisodium citrate | 29.0 g |
| 4. Sodium carbonate | 3.0 g |
| 5. Methyl paraben sodium | 3.0 g |
| 6. Deionised water | to 200 ml |

Ingredients 1, 2, 3, 4 and 5 were dissolved in item 6. 20 ml volumes of the solution were dispensed into 250 ml bottles containing 130 ml carbonated water, mixed and then fitted with air tight closures. Each bottle contained the equivalent to approximately 200 mg naproxen in a solution of pH approximately 6.0.

EXAMPLE 18
Preparation of a ready made effervescent pharmaceutical composition containing β-cyclodextrin/naproxen clathrate (0.9:1) without precomplexation

| | |
|---|---|
| 1. β-cyclodextrin | 10.4 g |
| 2. Naproxen | 2.0 g |
| 3. Trisodium citrate | 29.0 g |
| 4. Sodium carbonate | 3.0 g |
| 5. Methyl paraben sodium | 3.0 g |
| 6. Deionised water | to 200 ml |

Ingredients 1, 2, 3, 4 and 5 were dissolved in item 6. 20 ml volumes of the solution were dispensed into 250 ml bottles containing 130 ml carbonated water, mixed and then fitted with air tight closures. Each bottle contained the equivalent to approximately 200 mg naproxen in a solution of pH approximately 6.0.

EXAMPLE A
Reconstitution in water of a commercially available Ibuprofen tablet A Nurofen Soluble (trade mark) tablet containing ibuprofen (200 mg) was added to 150 ml of cold water. The tablet failed to completely dissolve, resulting in a white suspension.

EXAMPLE B
Reconstitution in water of a commercially available dispersible Naproxen powder The contents of a Naproxsyn (trade mark) sachet containing naproxen (500 mg) was added to 150 ml of cold water. The powder failed to completely dissolve, resulting in a white suspension.

EXAMPLE C
Preparation of an effervescent pharmaceutical composition containing Ibuprofen/βCD clathrate for reconstitution with cold water Ingredients 2 and 3 were seived through a 500 μm screen and mixed in a suitable mixer for 5 minutes. A small aliquot of water was added and the product was mixed for a further 5 minutes and then placed on stainless steel trays and dried for 2 hours at 60° C. The resulting granule was sieved through a 500 μm screen mixed for 5 minutes with ingredients 1 and 4 and then filled into sachets, (target fill weight 1.928 g) with each sachet containing the equivalent of 200 mg ibuprofen.

| | |
|---|---|
| 1. Ibuprofen/βCD clathrate from example 1 | 171.4 g |
| 2. Sodium bicarbonate | 11.6 g |
| 3. Citric acid (anhydrous) | 10.9 g |
| 4. Sodium carbonate (anhydrous) | 2.5 g |

The powder from one of the sachets was added to 150 ml cold water (16° C.) to give a suspension in which some of the ibuprofen/β-cyclodextrin clathrate remained undissolved.

EXAMPLE D
Preparation of an effervescent pharmaceutical composition containing Naproxen/βCD clathrate for reconstitution with cold water Ingredients 2 and 3 were seived through a 500 μm screen and mixed in a suitable mixer for 5 minutes. A small aliquot of water was added and the product was mixed for a further 5 minutes and then placed on stainless steel trays and dried for 2 hours at 60° C. The resulting granule was sieved through a 500 μm screen, mixed for 5 minutes with ingredients 1 and 4, and then filled into sachets, (target fill weight 2.62 g) with each sachet containing the equivalent of 200 mg naproxen.

| | |
|---|---|
| 1. Naproxen/βCD clathrate from example 4 | 106.0 g |
| 2. Sodium bicarbonate | 11.6 g |
| 3. Citric acid (anhydrous) | 10.9 g |
| 4. Sodium carbonate (anhydrous) | 2.5 g |

The powder from one of the sachets was added to 150 ml cold water (16° C.) to give a suspension in which some of the naproxen/β-cyclodextrin clathrate remained undissolved.

EXAMPLE E
The granulation and blending process described in Example 8 was repeated, except that the naproxen β-cyclodextrin was replaced with an equimolar quantity of naproxen sodium (10.95 g). The resulting powder was filled into sachets (target weight 5.219 g), with each sachet containing naproxen. (200 mg). The powder from one of the sachets was added to 150 mls cold water (16° C.) to give a suspension in which some of the drug remained undissolved.

EXAMPLE F

The granulation and blending process described in Example 8 was repeated, except that the ibuprofen β-cyclodextrin was replaced with an equimolar quantity of ibuprofen sodium (11.1 g). The resulting powder was filled into sachets (target weight 5.221 g), with each sachet containing ibuprofen (200 mg).

The powder from one of the sachets was added to 150 ml cold water (16° C.) to give a solution which initially had oily droplets floating on the surface. On standing, the droplets formed a white vitreous solid, containing undissolved ibuprofen.

EXAMPLE G

Preparation of an effervescent pharmaceutical composition containing Ibuprofen/βCD clathrate for reconstitution with cold water Ibuprofen sodium β-cyclodextrin complex (1:0.37) was prepared as described in GB 2,219,585 (Reckitt & Colman) Example 1. Ingredients 2 and 3 were seived through a 500 μm screen and mixed in a suitable mixer for 5 minutes. A small aliquot of water was added and the product was mixed for a further 5 minutes and then placed on stainless steel trays and dried for 2 hours at 60° C. The resulting granule was seived through a 500 μm screen, mixed for 5 minutes with ingredients 1 and 4 and then filled into sachets (target fill weight 5.6 g) with each sachet containing the equivalent of 200 mg ibuprofen.

| | |
|---|---|
| 1. Ibuprofen/βCD clathrate (1:0.347) | 30.0 g |
| 2. Sodium bicarbonate | 116.0 g |
| 3. Citric acid (anhydrous) | 109.0 g |
| 4. Sodium carbonate (anhydrous) | 25.0 g |

The powder from one of the sachets was added to 150 ml cold water (16° C.) to give a solution which initially had oily droplets floating on the surface. On standing, the droplets formed a white viscous solid containing undissolved ibuprofen. The pH of the mixture was approximately 6.1.

I claim:

1. A pharmaceutical composition, for oral consumption in aqueous solution, comprising a propionic acid NSAID/β-cyclodextrin clathrate, and a pharmaceutically acceptable acid-base couple, in a quantity sufficient to cause the propionic acid NSAID/β-cyclodextrin clathrate to dissolve when the composition is mixed with cold water and provide a solution with acid or neutral pH, wherein the weight of the acid-base couple is greater than 1% of the weight of water in which the composition is to be dissolved, and wherein the ratio of β-cyclodextrin to propionic acid NSAID is 0.8:1 to 10:1.

2. A pharmaceutical composition according to claim 1 wherein the drug is a lipophilic NSAID.

3. A pharmaceutical composition according to claim 2, wherein the drug is selected from the group consisting of ibuprofen, naproxen and ketoprofen.

4. A pharmaceutical composition according to claim 1, wherein the acid-base couple is an effervescent couple comprising a water soluble acidic substance, and a basic compound which, when combined, liberate carbon dioxide on neutralisation with acid.

5. A pharmaceutical composition according to claim 4, wherein the water soluble acidic substance is an edible organic acid.

6. A pharmaceutical composition according to claim 5, wherein the organic acid is selected from the group consisting of mono-basic, di-basic and tri-basic salts thereof.

7. A pharmaceutical composition according to claim 5, wherein the edible organic acid is selected from the group consisting of tartaric acid, citric acid and ascorbic acid.

8. A pharmaceutical composition according to claim 1, wherein the base is selected from the group consisting of alkali metal and alkaline earth metal carbonates, percarbonates and bicarbonates, and mixed carbonate salts.

9. A pharmaceutical composition according to claim 4 wherein the acid-base couple is an effervescent couple which comprises a water soluble acidic substance selected from the group consisting of citric and tartaric acid, and a base selected from the group consisting of sodium bicarbonate and carbonate.

10. A pharmaceutical composition according to claim 1 wherein the acid-base couple is a non effervescent couple comprising a water soluble acid and a conjugate base selected from the group consisting of sodium salt and potassium salt.

11. A pharmaceutical composition according to claim 10 which is administered as a solution in the pH range of about 4.0 to about 7.0.

12. A pharmaceutical composition according to claim 1, wherein the ratio of β-cyclodextrin to drug is about 1:1 to about 5:1.

13. A pharmaceutical composition according to claim 1, in a form selected from the group consisting of a tablet, a powder and granules for reconstitution with water, and ready-to-drink preparations.

14. A process for the preparation of a pharmaceutical composition as claimed in claim 1, which process comprises the admixture of a drug/β-cyclodextrin clathrate complex and an acid-base couple.

15. A method for oral dosing of a pharmaceutical composition according to claim 1, comprising administration of a therapeutically active dose of the drug as a complex with β-cyclodextrin in aqueous solution.

16. A pharmaceutical composition, for oral consumption in aqueous solution, comprising a drug selected from the group consisting of ibuprofen, naproxen and ketoprofen, β-cyclodextrin clathrate, and a pharmaceutically acceptable acid-base couple, in a quantity sufficient to cause the drug to dissolve when the composition is mixed with cold water and provide a solution with acid or neutral pH, wherein the weight of the acid-base couple is greater than 1% of the weight of water in which the composition is to be dissolved, and wherein the ratio of β-cyclodextrin to drug is 0.8:1 to 10:1.

17. A pharmaceutical composition, for oral consumption in aqueous solution, comprising a drug selected from the group consisting of ibuprofen, naproxen and ketoprofen, β-cyclodextrin clathrate, and a pharmaceutically acceptable acid-base couple, which comprises a water soluble acid and a conjugate base selected from the group consisting of sodium salt and potassium salt, in a quantity sufficient to cause the drug to dissolve when the composition is mixed with cold water and provide a solution with acid or neutral pH, wherein the weight of the acid-base couple is greater than 1% of the weight of water in which the composition is to be dissolved, and wherein the ratio of β-cyclodextrin to drug is 0.8:1 to 10:1.

18. A pharmaceutical composition, for oral consumption in aqueous solution, comprising a drug selected from the group consisting of ibuprofen, naproxen and ketoprofen, β-cyclodextrin clathrate, and a pharmaceutically acceptable acid-base couple, which acid component of the couple is edible organic acids, and their mono-di and tri-basic salts, and the base component of the couple is selected from the group consisting of sodium carbonate, percarbonate, bicarbonates, and mixed carbonate salts, in a quantity sufficient to cause the drug to dissolve when the composition is mixed with cold water and provide a solution with acid or neutral pH, wherein the weight of the acid-base couple is greater than 1% of the weight of water in which the composition is to be dissolved, and wherein the ratio of β-cyclodextrin to drug is 0.8:1 to 10:1.

19. A method for enhancing the solubility of propionic acid NSAID's in an aqueous solution which method comprises admixing an NSAID/β-cyclodextrin clathrate wherein the ratio of β-cyclodextrin to NSAID is 0.8:1 to 10:1; a pharmaceutically acceptable acid-base couple, wherein the weight of the acid-base couple is greater than 1% of the weight of cold water into which the composition is admixed, and which couple yields a solution with an acid or neutral pH.

20. The method according to claim 19 wherein the NSAID is ibuprofen, naproxen or ketoprofen.

21. The method according to claim 19 wherein the acid-base couple comprises a water soluble acid and a conjugate base selected from the group consisting of sodium salt and potassium salt.

22. The method according to claim 21 wherein the resulting pH of the cold aqueous solution is about 4.0 to about 7.0.

23. The method according to claim 19 wherein the molar ratio of β-cyclodextrin to NSAID is 1:1 to 3:1.

24. The method according to claim 19 wherein the maximum level of the acid-base couple is 15% of the weight of the water into which it is added.

25. The method according to claim 19 wherein the acid component of the couple is edible organic acids, and their mono-di and tri-basic salts, and the base component of the couple is selected from the group consisting of sodium carbonate, percarbonate, bicarbonates, and mixed carbonate salts.

26. The composition according to claim 16 wherein the drug is ibuprofen.

27. The composition according to claim 16 wherein the drug is naproxen.

28. The composition according to claim 16 wherein the drug is ketoprofen.

29. The composition according to claim 17 wherein the drug is ibuprofen.

30. The composition according to claim 17 wherein the drug is naproxen.

31. The composition according to claim 17 wherein the drug is ketoprofen.

32. The composition according to claim 18 wherein the drug is ibuprofen.

33. The composition according to claim 18 wherein the drug is naproxen.

34. The composition according to claim 18 wherein the drug is ketoprofen.

35. The method according to claim 20 wherein the drug is ibuprofen.

36. The method according to claim 20 wherein the drug is naproxen.

37. The method according to claim 20 wherein the drug is ketoprofen.

38. The composition according to any of claims 1 to 10, 11, 12 or 13, wherein the drug is ibuprofen.

39. The composition according to any of claims 1 to 10, 11, 12 or 13, wherein the drug is naproxen.

40. The composition according to any of claims 1 to 10, 11, 12 or 13, wherein the drug is ketoprofen.

* * * * *